United States Patent [19]

Cobben et al.

[11] Patent Number: 4,949,730
[45] Date of Patent: Aug. 21, 1990

[54] MONITORING DEVICE INTENDED ESPECIALLY FOR PARTURITION AND ITS APPLICATION

[76] Inventors: Andree Cobben; Francis Jaspar, both of 8 rue de Liernu, B-5854 Meux; Christian Mouthuy, Bte. 19, Avenue de Martin-Pecheur, B-1170 Bruxelles, all of Belgium

[21] Appl. No.: 351,106

[22] Filed: May 12, 1989

Related U.S. Application Data

[60] Continuation-in-part of Ser. No. 230,255, Aug. 9, 1988, abandoned, which is a division of Ser. No. 56,994, May 11, 1987, abandoned.

[30] Foreign Application Priority Data

Nov. 9, 1985 [LU] Luxembourg ............................ 86072
Mar. 9, 1986 [WO] PCT Int'l Appl. .... PCT/BE86/00027

[51] Int. Cl.⁵ ................................................ A61B 5/10
[52] U.S. Cl. ...................................... 128/775; 128/782
[58] Field of Search ............... 128/721, 733, 774, 775, 128/782

[56] References Cited

U.S. PATENT DOCUMENTS

3,520,294  7/1970  Fuzzell et al. ...................... 128/775

Primary Examiner—Randall L. Green
Assistant Examiner—Randy Shay
Attorney, Agent, or Firm—Fishman, Dionne & Cantor

[57] ABSTRACT

A monitoring belt which comprises at least one sensing element acting in the longitudinal direction of deformation of the belt enables abdominal muscular activity to be detected. The sensing element is connected to an electronic circuit for evaluation, treatment and/or recording of data supplied by the sensing element. The resultant evaluation enables an alarm or safety system to be triggered.

5 Claims, 5 Drawing Sheets

MONITORING DEVICE INTENDED ESPECIALLY FOR PARTURITION AND ITS APPLICATION

This is a continuation-in-part of U.S application Ser. No. 230,255 filed Aug. 9, 1988, now abandoned, which is a divisional of U.S. application Ser. No. 056,994 filed May 11, 1987, now abandoned.

OBJECT OF THE INVENTION

The present invention relates to a reliable method for monitoring parturition in animals and in human beings. It also relates to a device for carrying out the said monitoring and to the application of this method and of this device in human or veterinary medicine or in livestock breeding.

The invention will be described hereinafter essentially as it relates to the parturition of animals but this does not exclude, with adaptation if required, its use in human beings.

The development of increasingly efficient breeds of animals generally goes hand in hand with the need for outside assistance during parturition. This implies the requirement on the part of the breeder of monitoring his animal so closely that it is almost certain that he will be present during delivery to assist himself or to call for veterinary help, at the right time. In some cases, not being present at the critical moment leads to the death of the newborn and sometimes even to that of the mother. The economic consequences of this phenomenon are obviously very heavy for the breeder to bear.

In human obstetrics, more elaborate human and material resources are employed; nevertheless, a device which enables the process of childbirth to be monitored in an objective way is of great potential value, possibly in addition to other techniques such as echography.

SUMMARY OF THE STATE OF THE ART

In the vast majority of cases, breeders monitor their animals in a subjective way and take into account visible features such as, for example, the degree of irritability, the shape of the pelvis, the position of the tail etc. in order to judge whether the animal is likely to give birth during the next few hours. This examination will be repeated very many times, day and night, during the few days which precede delivery.

Nevertheless, monitoring systems which supplement the purely subjective monitoring already exist.

A system described in the document FR-A No. 2,413,875 enables a critical moment to be detected: that of the appearance of the waters during the rupture of the bag of waters in the birth process The latter system has the advantage of monitoring the animal in an objective way. However, it suffers from two major disadvantages:

(1) The detecting device is intra-vaginal and thus causes the animal discomfort and it exposes it to the risk of infections and is difficult for the breeder to use;

(2) The device is not totally reliable because it is known to the specialists that a large proportion of animal parturitions takes place without significant flow of waters before the birth or without the flow being detected by the system.

Other invasive techniques, that is with intravaginal action, have been described especially in the patents BE-A Nos. 852,331, 873,572, 892,016, FR-A Nos. 2,218,870, 2,226,489, 2,413,875 and 2,565,097, EP-A No. 0,108,330 and DE-A No. 2,416,829.

Several non-invasive techniques which are based on the observation of phenomena associated with parturition have also been described.

Some of these are based on the position chosen by the animal. This is the basis, for example, in the case of patents DE-C No. 2,712,854, WO-A No. 82/00952, BE-A No. 830,865, U.S. Pat. No. 4,055,839, NL-B No. 7,906,774.

Another technique consists in detecting the presence of the young after expulsion (FR-A No. 2,241,239) or this expulsion itself (U.S. Pat. No. 4,232,686, FR-A Nos. 2,349,318, 2,353,225, 2,514,635, GB-A No. 632,827, BE-A No. 864,477).

Finally, FR-A No. 2,389,368 measures the moisture of sudation during delivery and BE-A No. 867,412 the horizontality of the animal's tail over a period of time longer than normal.

In human obstetrics, the document U.S. Pat. No. 4,299,233 describes the measurement of body vibrations by the determination of sound waves in a mattress or cushion filled with a liquid. Of course, there are also a echographic devices for monitoring childbirth.

All these techniques have a series of disadvantages which are, moreover, largely described in the documents mentioned themselves.

These disadvantages may be summarized by their low reliability, the laboriousness of setting them up, the risk of false alarms resulting from the movement of the animal, the discomfort for the animal resulting in the animal trying to free itself of the device, for example, by rubbing, and for some of them, their high cost price.

Finally, most of the known devices can be transferred from one species of animal to another only with difficulty and often require even a specific adaptation for each type of animal, even for each particular animal.

OBJECT OF THE INVENTION

As a result of what has been said above, and for reasons of economical yield related to a reduction in the loss of animals through death, through wounding or through any other devaluation and to a decrease in the manpower required for the subjective monitoring, there is considerable demand for a method and for a device for a reliable monitoring of parturition in animals. For the human species, any technique which can be used in addition to known means is, of course, highly desirable and is of obvious interest.

The invention aims at providing such a method and device which eliminates to a large extent the major disadvantages of the solutions offered by the state of the art.

CHARACTERISTIC FEATURES OF THE INVENTION

The solution provided by the invention rests on the observation that muscular activity in the abdominal region, which is directly or indirectly due to contractions, forms one of the most significant signs of the process of parturition.

The present invention proposes, inter alia, a monitoring method for animals and human beings which consists in detecting, monitoring and/or recording abdominal muscular activity and, in particular, uterine and abdominal contractions and subsequently, in following the changes in the amplitude and the frequency thereof.

The device for the implementation of this method consists of a belt which incorporates a sensing element operating in the longitudinal direction of deformation of the said belt with a view to measuring the said muscular activity related to uterine and abdominal contractions.

A particular problem with this type of belt can be illustrated by the following example. Supposing that a belt equipped with instruments has been set in position, on an animal in the standing position, if the latter lies down, the natural deformation of the body in this new position will result in a signal as a consequence of tension in the belt. This signal must be distinguished from the warning signal resulting from uterine and abdominal contractions. To this end, the device is equipped, according to one characteristic, with a unit for appropriate electronic processing of the signals, the details of which will be described below.

This electronic unit comprises at least the following components: amplifier, filters, analogue-digital converter, microprocessor and storage.

The electronic processing unit, using a technique of storing of the base line, makes it possible to determine at any moment and during any new stress, whether it is a signal which has a new spectrum the general pattern of which is that of a uterine and abdominal contraction. The unit could, as soon as this identification is made, store the contraction and its parameters and trigger an alarm, especially the breeder's safety system, in the case where the contractions detected have changed in their number and/or their frequency and/or their amplitude.

The sensing element of the monitoring belt can be a piezoelectric plastic sheet.

The piezoelectric phenomenon, that is, the creation of electrical charges under the influence of a mechanical deformation and vice versa has been known for many decades in inorganic materials such as, for example, quartz or ceramics containing oxides of lead, zirconium, barium, titanium, etc.

These materials are generally expensive, fragile and exist only in small surface areas which implies that they must be handled with care when they are used as detectors.

Recently, some laboratories have developed piezoelectric organic materials the best-known of which is PVDF (polyvinylidene fluoride). However, there are others, and especially compounds containing coated piezoelectric ceramic particles in a polymer matrix.

For the application which forms the subject of the invention, it is advantageous to use a plastic piezoelectric element, for the following reasons:

(1) elasticity: as the piezoelectric element can be a sheet as thin as 10 to 20 microns, it has a flexibility such that, even over a large surface area, it will adapt itself closely to the shape of the animal, (2) large surface area: the fact that the sensing element may be chosen to have a large surface area (for example, a 5 to 10 cm wide strip all along the side of the subject) means that the setting in position of the belt for use is made easy;

(3) sturdiness: a piezoelectric film ensures a high resistance to consecutive impacts and shocks while setting up the belt or during its use (rubbing of the animal against walls, beams etc. which are present in its surroundings).

The piezoelectric sheet is rigidly fixed at its ends to the belt which holds it in position by means of adhesive or other mechanical means of fixing.

The belt will advantageously consist of a synthetic fibrous material (for example, made of polyester) which ensures a degree of elasticity, but it may also comprise a nondeformable part and an elastic part.

The contact wires required are made integral with each of the two electrodes present on either side of the sensing film, for example, by means of conducting adhesives.

In order to ensure the mechanical and chemical protection of the whole, the entire sensing element is covered with a sheet of plastic such as, for example, unpolarized PVDF or PTFE.

In such a configuration, an electrical signal will be recorded for each strain exerted in a direction perpendicular or longitudinal to the piezoelectric sheet.

Removal of interferences effecting detection, such as, for example, production of pyro-electrical signals or the production of signals due to movements of the subject under observation may be achieved by any suitable means, especially by using two sensing elements per detector.

In this configuration, only one of the piezosensing elements is exposed to disturbances created by the parameter measured, whereas the other element is exposed to all other common stimulations. By a parallel connection of transducers or by an appropriate processing of the data, all the signals which are common to those elements will cancel themselves out.

The piezo-sensing element can simultaneously record many of the parameters such as, for example, cardiac and respiratory cycles and/or arterial pressure and this is done either by using a single transducer the signals of which are analysed together and resolved by the electronic processing unit, or alternatively, by arranging along the circumference of the belt as many piezo-sensing elements as there are functions to be followed and by processing each of the signals detected in a separate unit.

A temperature sensor, such as, for example, a thermocouple or a thin-layer platinum resistance probe may be incorporated into the belt, in order to record the body temperature of the subject as well.

Instead of using piezoelectric plastic films, the sensing element of the belt may also be a piezosensing rubber film or a strain gauge or a deformable chamber and a pressure sensor.

Piezo-sensing rubbers such as, for example, silicones fitted with electrically conducting particles and the electrical resistivity of which is significantly modified when mechanical deformations are imposed on an element of this material are currently available.

On connecting the piezoresistive element to a Wheatstone bridge energized with a direct current, the application of a deformation of the belt will lead to a change in the output voltage of the bridge.

Strain gauges are currently used in applications as varied as the analysis of stresses and of deformations in mechanical or civil engineering structures or also as the sensing element in sensors such as, for example, force, deformation or pressure sensors.

The gauges are in general deposited on a support like glass or polymers such as, for example, polyimides.

There are different types of gauge materials. Roughly, they can be divided into three groups:
 (1) metal gauges;
 (2) semiconductor gauges;
 (3) metal-ceramic gauges (CERMET).

Metal gauges are by far the most common.

The operating principle of the gauges is piezoresistive, that is, any mechanical stress imposed on the gauge results in a deformation which itself results in a change in the nominal electrical resistance of the gauge.

The gauges are characterized mainly by the gauge factor defined as:

$$k = \frac{\Delta R \cdot 1}{R \epsilon},$$

where
R is the nominal resistance,
ΔR, the change in resistance, and
ε, the relative deformation (ΔL)/(L).

The metal gauges generally have a gauge factor of 2, the CERMET gauges, 15, and the semiconductor gauges, 80.

Consequently, these latter facilitate the detection of changes in resistance, the change in resistance at equal deformation being approximately 40 times greater.

Nevertheless, the metal gauges remain the most used because they are the most stable and the least dependent on the ambient temperature.

The changes in resistance are generally measured using a Wheatstone bridge which, when this latter is fed with a d.c. voltage, enables the voltage of imbalance of the bridge resulting from the change in the resistances forming the bridge to be measured.

When a deformable chamber containing a fluid such as air, for example, and a pressure sensor is used, any deformation undergone by the belt will result in a change in volume of the deformable chamber. This latter will produce a change in the internal pressure, which, in its turn, will be detected by the pressure sensor.

An additional characteristic of the present invention lies in the use known per se, in the meantime, of radio links between the "monitored" subject (animal or human) and the person monitoring (breeder or keeper) or between the subject monitored and a data processing station of an emergency point.

From a purely technical point of view, it is important to take into account the fact that the invention has the following advantages:

an active belt which combines an elastic component and the transmission of loading at the same time, cancellation of static components (position of the subject or of the belt, long period signals) by an automatic correction of the offset, and analysis by one and the same belt of several parameters enabling a correlation of the signals recorded to be carried out.

By virtue of its design, the belt of the invention, because it works longitudinally, further offers the advantage that the position of the sensing element relative to the zone monitored is relatively unimportant.

Thus, a uterine contraction may be measured with a belt equipped with instruments covering the ventral part of the subject, but with the sensing element being positioned on the back of the subject.

Similarly, the heartbeat can be detected in addition, with a belt equipped with instruments which is attached in the cardiac region, but with the sensing element not being positioned in front of the heart.

Compared with the existing solutions, this advantage offers the following obvious practical benefits:

setting up and positioning of the equipment is not difficult and can be carried out by unqualified staff, possibility of carrying out mobile measurements without difficulty.

BRIEF DESCRIPTION OF THE DRAWINGS

Referring now to the drawing wherein like elements are numbered alike in the several FIGURES.

DESCRIPTION OF THE PREFERRED EMBODIMENTS

Figure 1:
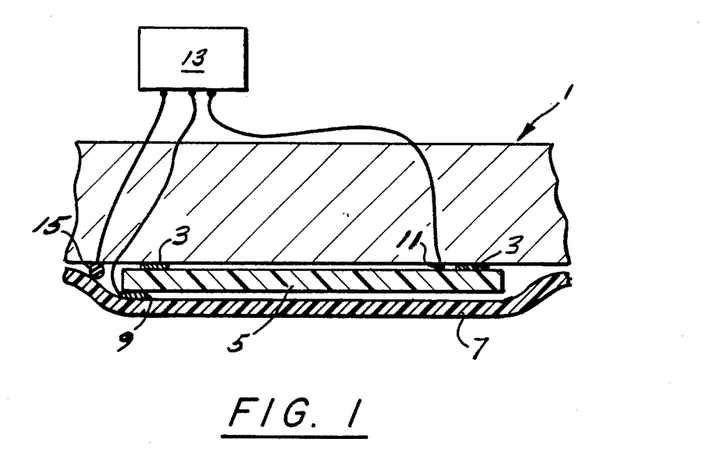
FIG. 1 is a diagrammatic cross sectional view of a monitoring belt in accordance with the present invention.

In the drawings attached, FIG. 1 represents a diagrammatic cross-section of a monitoring belt.

This belt 1 which surrounds the sides or the thorax of the animal or of the human being comprises appropriate means 3 for attaching a piezo-sensing element 5, preferably covered with a protective film 7, as mentioned above.

Contacts 9 and 11 are connected by wires to an electronic processing unit shown diagrammatically by a block 13.

Additionally, a temperature probe 15, also connected to the block 13, is shown by way of illustration.

Figure 2:
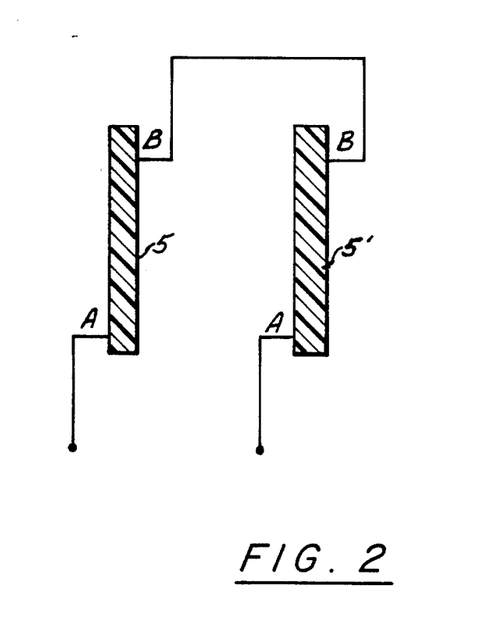
FIG. 2 is a diagram depicting two piezoelectric elements in parallel.

FIG. 2 represents the diagram of an equalizing electrical connection of two piezoelectric elements in parallel. Two piezo-sensing elements 5 and 5' are mounted in parallel as shown. One of the elements is arranged so that it is necessarily sensitive to the parameters monitored, whereas the other is arranged so as not to be subjected to these. All the interference signals not resulting from the parameters monitored (for example, the animal rubbing against its stall) will therefore be sensed by the components 5 and 5' and will cancel themselves out. In contrast, the parameters monitored, sensed necessarily by only one of the two elements, will give a useful signal.

Figure 3:
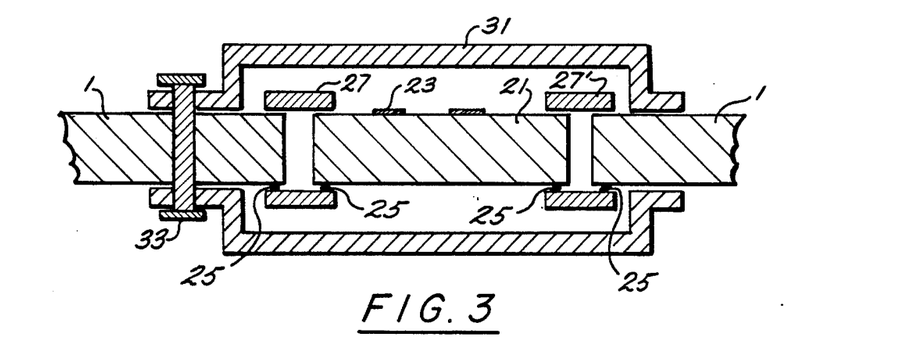
FIG. 3 is a diagrammatic view of a monitoring belt having strain guages.

FIG. 3 represents a diagrammatic view of the monitoring belt comprising strain gauges as the sensing element.

In this case, the belt 1 consists of a slightly deformable or nondeformable material (for example, a textile) and a deformable element 21 on which the piezoresistors 23 are arranged and which is attached rigidly to the belt by a fastening or an adhesive 25 and two fasteners 27 and 27'.

The deformable element 21 could be, for example, an elastomer, or alternatively a thin metal sheet.

Figure 4:
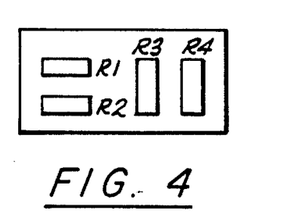
FIG. 4 is a schematic view depicting an arrangement of piezoelectric elements.

The piezoelements ($R_1$ to $R_4$) are arranged as shown in FIG. 4 in order to maximize the change in resistance and to minimize the interferences such as, for example, a temperature change.

Figure 5:
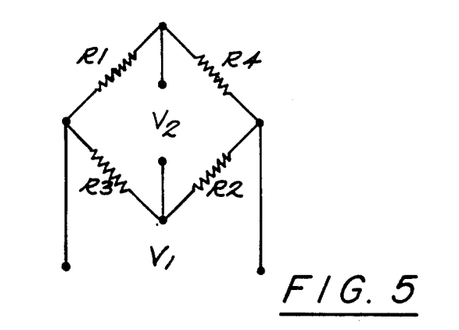
FIG. 5 is a schematic of a wheatstone bridge.

Piezoelements are connected into a Wheatstone bridge as shown in FIG. 5, with the input $V_1$ and the output $V_2$.

In order to avoid an excessive deformation of the piezoresistors, the deformable region of the belt is equipped on either side with a metallic protecting collar 31 retained by a fastening 33. This prevents:

(1) an excessive deformation by perpendicular stimulation or deformation, (2) an excessive longitudinal deformation.

This last function is achieved, for example, in the following way.

The cover 31 is fixed to the belt on only one side of the sensing element with the fastening 33. On the other side, the cover may slide on this latter as shown. The fastener 27' which connects the deformable element to the belt which will serve (on the unfixed side) as the stop for the longitudinal deformation.

Figure 6:
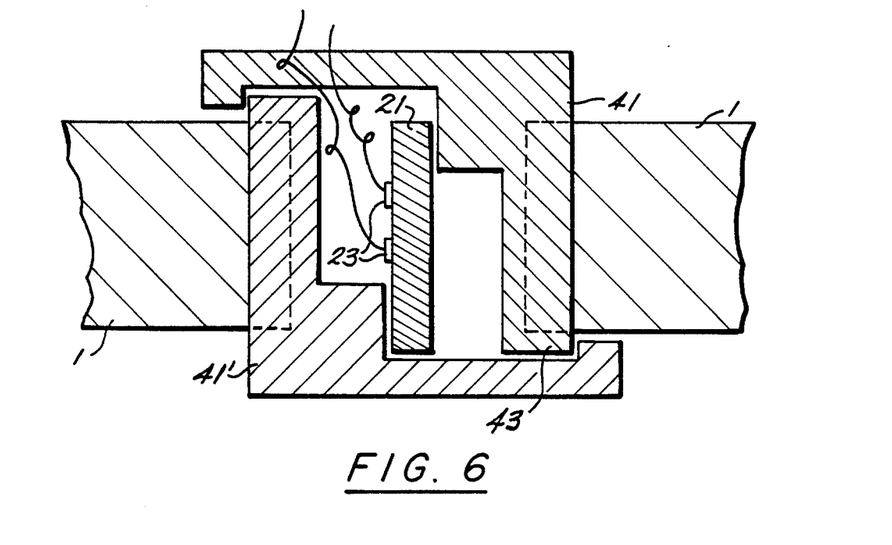
FIG. 6 is a diagrammatic cross-sectional view of a monitoring belt in accordance with another embodiment of this invention.

FIG. 6 represents another configuration of the belt equipped with strain gauges.

In this case, the deformable element 21 which supports the strain gauge 23 is arranged so that the longitudinal deformations are converted into transverse deformations in the deformable element.

This configuration enables a relatively rigid deformable support to be used, ensuring a relative deformation which is suitable for the measurement at the same time.

As shown in FIG. 6, the longitudinal deformation of the belt 1 is transmitted to the deformable element 21 by means of two rigid armatures 41 and 41' fixed rigidly to each end of the belt 1 and exerting a bending strain on the deformable element 21.

The deformation armatures are additionally equipped with an arm 43 serving as stop for the other armature and thus preventing excessive extensions during the setting in position or during storage of the equipment.

Thus, the structural shape of FIG. 3 is essentially provided for working in longitudinal deformation and that of FIG. 6 for working essentially in the transverse deformation.

Figure 7:
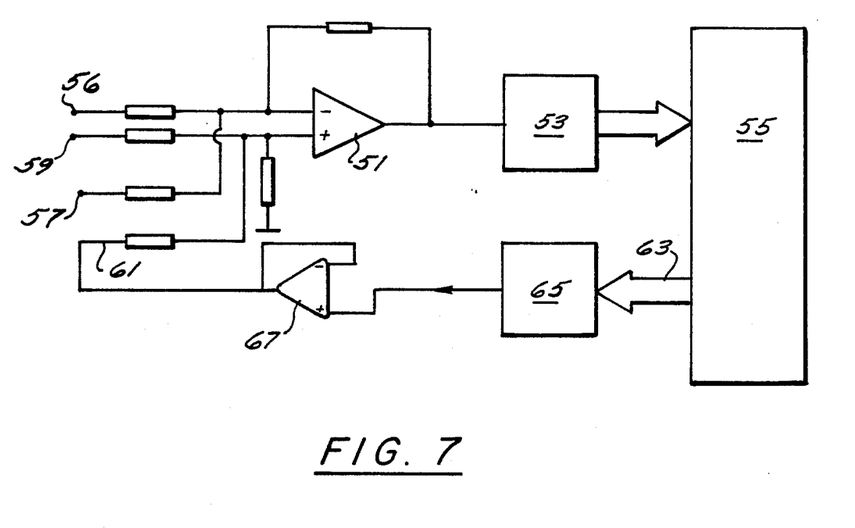
FIG. 7 is a schematic of a processing circuit for use in the present invention.

A structural shape of an electronic processing circuit according to the invention is described below, with the help of FIG. 7, by way of example.

According to the invention, the electronic processing circuit comprises at least one means for the amplification of the signal, a means for the differentiation of the signal sensed among interferences and a means for the automatic correction of the base line of signals.

By reference to this figure, the electronic processing circuit essentially comprises an amplifier for input signals assembled as a differential amplifier 51 and if appropriate a high-gain amplifier mounted downstream of the latter, the signals of which are directed to an analogue-digital converter 53 to be processed by a processing unit 55 such as a microprocessor. The various outputs (not shown) of the microprocessor are used for controlling some related functions and for controlling alarm equipment etc. Related functions means the automatic correction of the base line, power supply voltage regulation and other functions.

Figure 11:
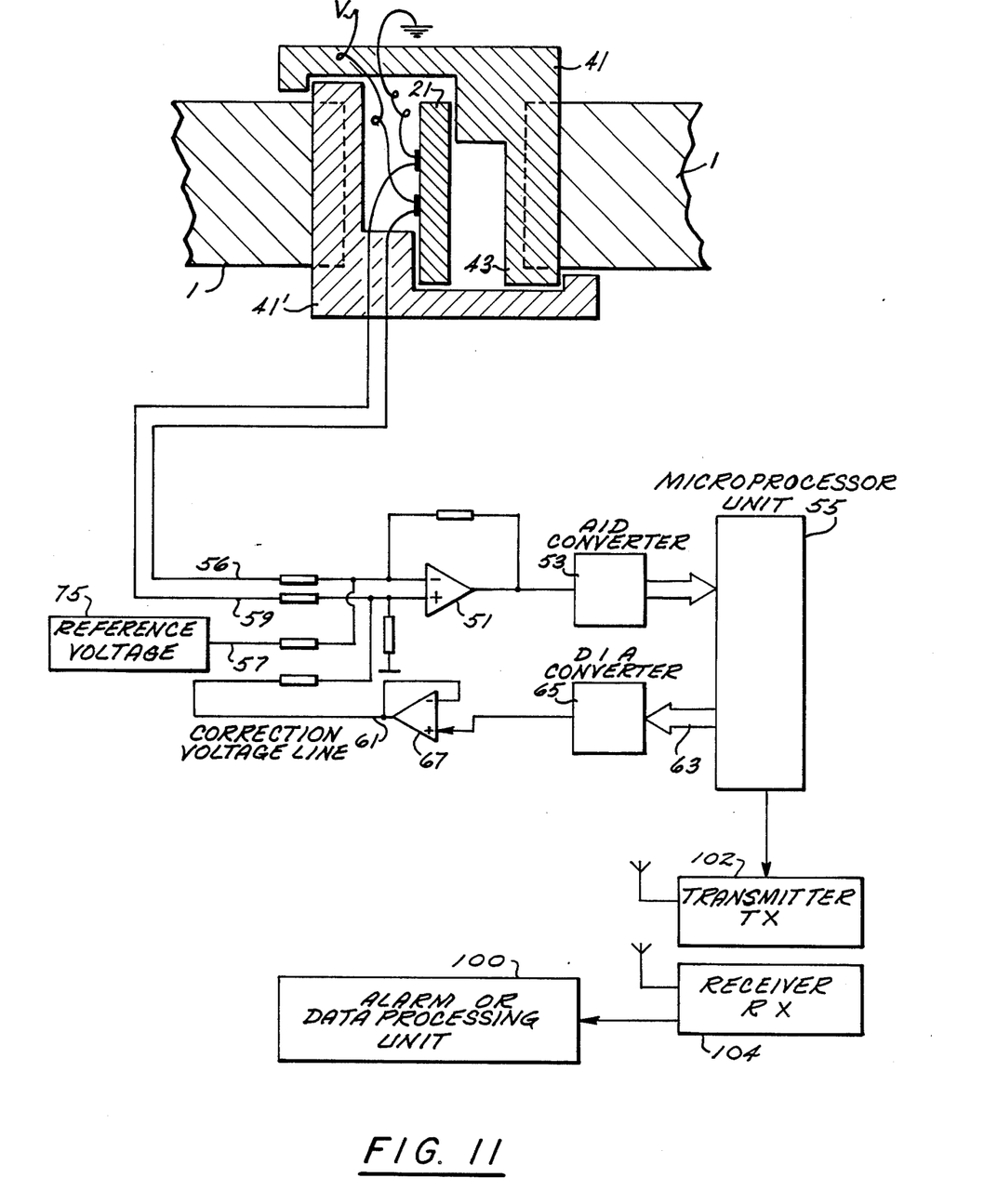
FIG. 11 is diagrammatic view combining the subject matter of FIGS. 6 and 7.

Advantageously, (and referring to FIG. 11 which is a combination of FIGS. 6 and 7) the probe signal line 56 mounted in parallel is connected to a reference voltage 57 before being connected to the first input of the differential amplifier 51. Similarly, the measuring probe signal line 59 is connected to the base line correction voltage 61 before being connected to the second input of the differential amplifier 51. FIG. 11 clearly depicts an important feature of this invention wherein sensing element signal line 56 is connected to a reference voltage 75 (and 57) upstream of a first input to differential amplifier 51 and sensing element signal line 59 is connected to base line correction voltage 61 upstream of a second input to differential amplifier 51.

Computer software is used for computing the average activity sensed by the sensing element during the monitoring. This average activity represents the behavior of the subject under monitoring. This activity is considered as noise as opposed to parturition signals. This noise figure is representative of the baseline of the patient activity under normal living conditions. This baseline does not include the parturition signals and is therefore not relevant as useful information for detecting the parturition sequences. In order to only process the parturition sequence signal, the baseline activity must be therefore substracted from the sensing element signals. This is performed by generating a new control value from the baseline. This control value is fed back into the input amplifier by a D/A converter.

The above-described computer software thus makes it possible to perform a series of functions listed below in a non-limiting initial checking of the static stress in the belt in order to validate setting up on the subject to be examined, reading the sequential signals, filtering the signals measured, calculation of the new control value for the base line and the automatic adjustment of the position of the latter, identification of abdominal and/or uterine contractions, analysis for the contraction parameters, triggering an alarm when one of the following phenomena is recognized;

first uterine contractions, appearance of the first abdominal contractions, appearance of the first expulsive contractions, non-appearance of one or the other of these phenomena after a certain time lapse, tests on the operation of the sensor and emission of signals in case it is faulty.

Still referring to FIG. 11, the output 63 of the microprocessor 55 intended for the correction of the base line is connected to a digital/analog converter 65 which is connected (61), if required, through an amplifier 67, to the differential amplifier 51.

FIG. 11 also depicts a wireless connection between microprocessor 55 and either a data processing station or an alarm identified at 100. The wireless communication means includes a transmitter 102 and a receiver 104 which may operate in any known manner including radio waves, infrared or by ultrasonics. Receiver 104 may be stationary or portable.

Figure 8:
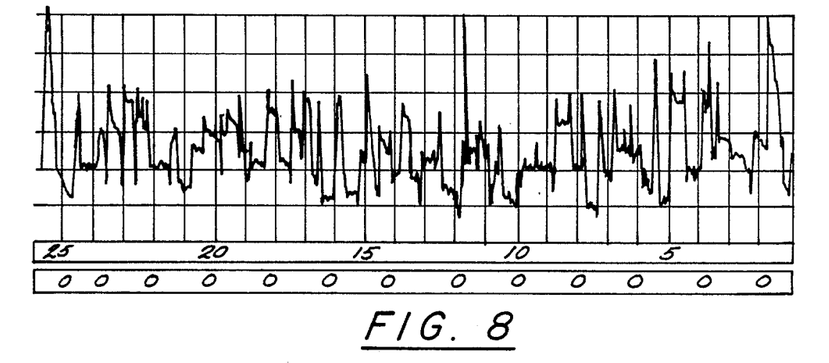
FIGS. 8, 9 and 10 are graphs depicting analysis made by the monitoring belt of this invention.
Figure 9:
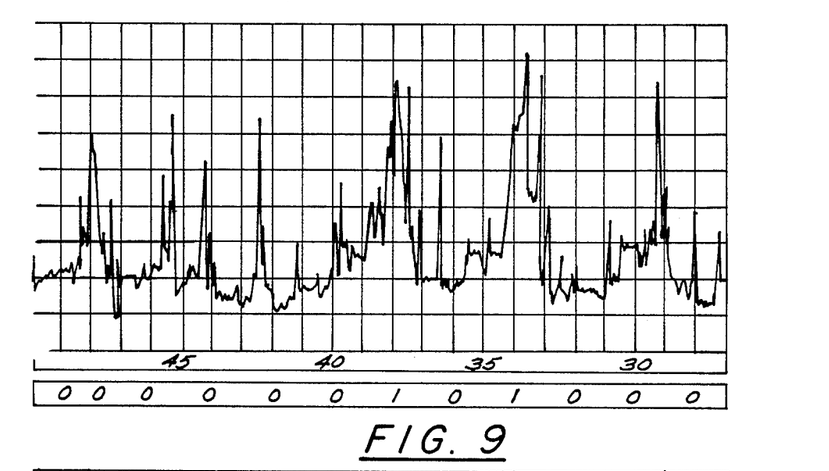
Figure 10:
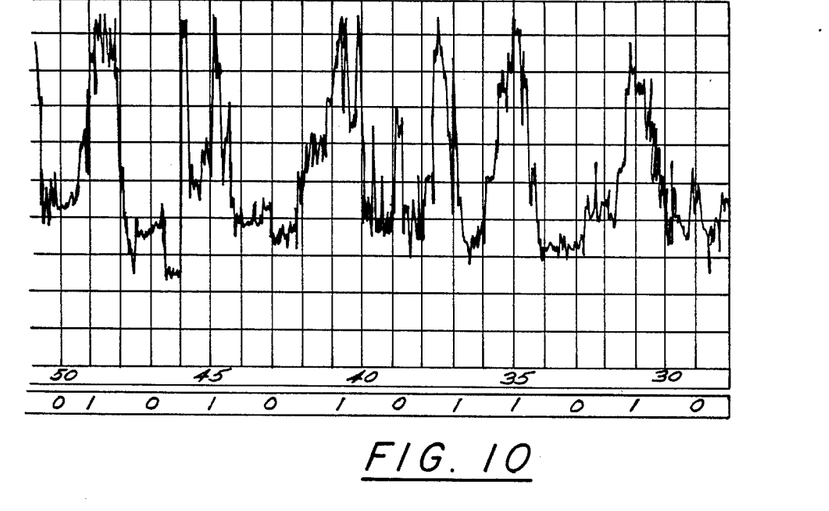

FIGS. 8, 9 and 10 represent a sequence of the parameter analyzed, obtained by making a representation in series of the phenomena detected. A register is incremented by a value of "1" or "0" depending on whether a phenomenon has been detected or not. A comparative and differential study enables the changes in the phenomenon to be evaluated.

In FIG. 8, no distinguishing effect is yet detected in the graph.

In FIG. 9, the start of intense activity is observed and in FIG. 10, the activity is very intense.

Many other embodiments are, of course, possible within the scope of the invention.

In the drawings, identical reference points have been used for components which are similar in function, but not necessarily identical. The choice of materials employed will, of course, be adapted in each case to the stresses to be withstood and to the functions to be carried out.

By way of examples, two possible configurations for the use of the monitoring belt are described.

EXAMPLE 1

The belt as represented in FIGS. 1, 3 and 6 is equipped with an autonomous electronic processing unit powered by cells or by a battery. The unit enables the first uterine and/or abdominal contractions to be detected and at this moment, an alarm signal is sent out by radio waves from the processing unit to a portable receiver which is continually carried by the breeder or the keeper.

EXAMPLE 2

The belt is equipped with a preprocessing (amplifier) unit which sends radio waves of the signals received to a central processing unit situated not far from the subject being monitored and which can process signals coming from several monitoring belts.

As soon as the central unit records a critical observation, a signal is sent either to a central alarm, or to radio receivers carried by the keeper and his staff.

While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. Parturition monitoring device comprising:
   a monitoring belt which comprises two sensing elements acting in the longitudinal direction of deformation of said belt which enables abdominal muscular activity to be detected, said sensing elements being connected to an electronic circuit for evaluation, treatment and/or recording of data supplied by said sensing elements, said evaluation treatment and/or recording enabling an alarm or safety system to be triggered, said two sensing elements being mounted on said belt so that only one of the sensing elements is exposed to disturbance produced by parameters to be monitored, whereas the other element is exposed to all other common stimulations, said two sensing elements being connected so that all signals common to said two sensing elements cancel themselves out;
   wherein said electronic circuit comprises;
   a microprocessor and storage means;
   a differential amplifier for receiving input signals;
   a first sensing element signal line mounted in parallel to and being connected to a reference voltage upstream of a first input to the differential amplifier;
   a second sensing element signal line being connected to a base line correction voltage upstream of a second input to the differential amplifier;
   analog to digital conversion means connected between the differential amplifier and the microprocessor;
   digital to analog conversion means connected to the microprocessor; and
   at least one amplifier means connected between the digital to analog conversion means and the base line correction voltage, the base line correction voltage being supplied by the microprocessor after analog/digital conversion and analysis.

2. Device according to claim 1 further comprising:
   said sensing elements being adapted for location in a abdominal or thoracic region of a body which enables at least one of the parameters of body temperature, respiratory cycle, cardiac cycle and arterial pressure to be recorded.

3. Device according to claim 1 wherein said belt at least partially comprises:
   a synthetic fiber which ensures a degree of elasticity, and wherein said sensing elements are rigidly fixed at its ends to said belt which ensures the support thereof by means of adhesives or other mechanical fastening means.

4. Device according to claim 1 wherein said sensing elements of said monitoring belt is selected from the group comprising:
   a piezoelectric plastic sheet, PVDF (polyvinylidene fluoride), compounds containing coated piezoelectric ceramic particles in a polymer matrix, a piezosensing rubber film, at least one strain guage, a deformable chamber containing a fluid and a pressure sensor.

5. Device according to claim 1 including:
   wireless connection means for connection between said microprocessor and a data processing station, an alarm or a receiver.

* * * * *